United States Patent [19]

Lascombes

[11] Patent Number: 5,318,750
[45] Date of Patent: Jun. 7, 1994

[54] DEVICE FOR THE PREPARATION OF A SOLUTION FOR MEDICAL USE

[76] Inventor: Jean-Jacques Lascombes, 21, Rue d'Orlèans, 31000 Toulouse, France

[21] Appl. No.: 17,153

[22] Filed: Feb. 12, 1993

[30] Foreign Application Priority Data

Feb. 14, 1992 [FR] France .................. 92 01851

[51] Int. Cl.⁵ .................. A61M 1/16; B01F 5/10
[52] U.S. Cl. .................. 422/81; 422/82; 422/82.02; 422/110; 137/268; 210/646; 210/647; 366/152; 604/4; 604/5; 604/6
[58] Field of Search .......... 422/81, 82, 82.02, 101, 422/110, 278, 279, 44; 137/268; 366/152, 172, 177, 178; 210/645–647; 604/4, 5, 6

[56] References Cited

U.S. PATENT DOCUMENTS

| | | | |
|---|---|---|---|
| 4,158,034 | 6/1979 | Riede et al. | 422/36 |
| 4,784,495 | 11/1988 | Jonsson et al. | 366/151 |
| 5,173,125 | 12/1992 | Felding | 134/22.11 |

FOREIGN PATENT DOCUMENTS

| | | | |
|---|---|---|---|
| 0278100 | 8/1988 | European Pat. Off. | A61M 1/16 |
| 0401130 | 12/1990 | European Pat. Off. | A61M 1/14 |
| 0439793 | 8/1991 | European Pat. Off. | A61M 1/16 |
| 0443324 | 8/1991 | European Pat. Off. | B01F 5/10 |
| WO8600797 | 2/1986 | PCT Int'l Appl. | |

Primary Examiner—James C. Housel
Assistant Examiner—David Redding
Attorney, Agent, or Firm—Keck, Mahin & Cate

[57] ABSTRACT

A device for the extemporaneous and continuous preparation of a solution for dialysis by the dissolution of several substances in powder form in water. The device includes a number of independent cartridges each containing a salt of a substance necessary for the preparation of the dialyzate, such as sodium chloride, potassium chloride, calcium chloride, magnesium chloride, and sodium bicarbonate. The device includes at least one first conduit communicating with an inlet to the cartridges for introducing water into the cartridges to produce aqueous solutions in said cartridges, at least one second conduit communicating with an outlet from said cartridges for bringing the aqueous solutions to mixing point located upstream from a dialysis circuit, a first measurement device mounted on the second conduit upstream from the mixing point, for measuring the concentration of the aqueous solutions at the outlet of the cartridges, a second measurement device mounted downstream from the dialysis circuit, and at least one flow-rate regulating device for regulating the flow rate of the water to modify the concentration of the aqueous solutions in response to the information provided by the first and second measurement devices.

18 Claims, 1 Drawing Sheet

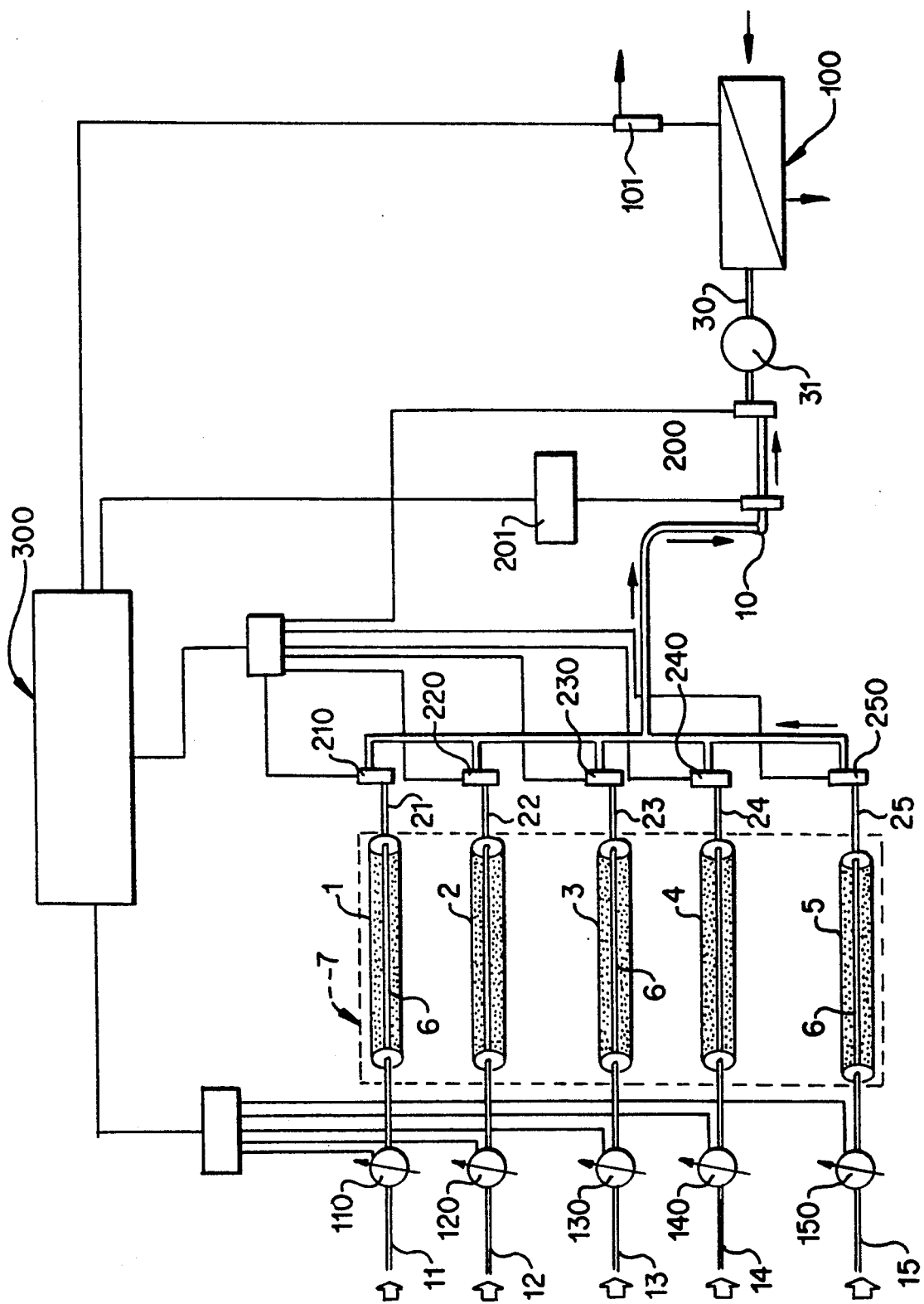

DEVICE FOR THE PREPARATION OF A SOLUTION FOR MEDICAL USE

FIELD OF THE INVENTION

The present invention relates to a device for the preparation of a solution for medical use by the dissolution of several substances in powder form in a carrier fluid; more particularly, but not specifically, it relates to a device for the preparation of a solution for dialysis.

BACKGROUND OF THE INVENTION

In order to conduct a hemodialysis session, it is necessary to use an apparatus known as a generator. In this type of apparatus, one uses a carrier fluid, which is generally purified water; the preparation of the dialyzate is done from concentrates in liquid or powder form, which are diluted in this carrier fluid.

The use of generators of this type thus requires transport of large volumes of previously prepared products to the treatment sites, along with their storage at the sites under consideration; these constraints are the source of the high operational costs.

SUMMARY OF THE INVENTION

The device of the invention particularly allows one to eliminate this phase of preparation. In effect, it allows the dialyzate to be prepared in a [production] line, allowing for continuous testing and possible instantaneous modification of the concentration of the different aqueous solutions included in the concentration.

In a general way, the invention thus relates to a device for the preparation of a solution for medical use by the dissolution of several substances in powder form in a carrier fluid; said device includes:
- a number of cells, each containing at least one of said substances in powder form,
- at least one first conduit that communicates with said cells in order to introduce said carrier fluid into said cells so as to produce aqueous solutions in said cells,
- at least one second conduit that communicates with said cells in order to bring said aqueous solutions produced in said cells to a site of utilization,
- at least one measurement means mounted upstream from said site of utilization, for measuring the concentration of said aqueous solutions produced in said cells, and
- at least one means of flow-rate regulation for regulating the flow rate of said carrier fluid in order to modify the concentration of said aqueous solutions in said cells in response at least to the information provided by said measurement means.

The device as defined above can be applied particularly advantageously to the extemporaneous and continuous preparation of a solution for dialysis by the dissolution of several substances in powder form in water; said device includes:
- a number of independent cartridges, each containing a salt of a substance necessary for the preparation of the dialyzate, such as sodium chloride, potassium chloride, calcium chloride, magnesium chloride, and sodium bicarbonate,
- at least one first conduit that communicates with an entrance to said cartridges in order to introduce water into said cartridges so as to produce aqueous solutions in said cartridges,
- at least one second conduit that communicates with an outlet from said cartridges in order to bring said aqueous solutions to a mixing point upstream from a dialysis circuit,
- a first measurement means mounted on said second conduit upstream from said mixing point, for measuring the concentration of said aqueous solutions in said cartridges,
- a second measurement means mounted downstream from said dialysis circuit, and
- at least one means of flow-rate regulation for regulating the flow rate of the water in order to modify the concentration of said aqueous solutions in response to the information provided by said first and second measurement means.

According to a particularly advantageous characteristic of the invention, above-said cells or cartridges contain a means of diffusion and of circulation of the carrier fluid or the water in said cells or cartridges.

This means, which allows one to introduce water into the volume of powder contained in the cartridges and to facilitate obtaining concentrated solutions, consists of at least one semipermeable membrane fiber, essentially arranged along the longitudinal axis of said cartridges between the entrance and outlet of these cartridges.

Quite obviously, these cartridges are delivered in dry and sterile form, which eliminates any risk of contamination. Moreover, the powder form used with these cartridges is a very stable form from a physicochemical as well as bacteriological standpoint.

Other characteristics and advantages of the present invention will emerge from reading the following description of an example of a device for the preparation of a solution for dialysis according to the first teachings given above; this example is given simply as an illustration and no interpretation restricting the desired protection can be extracted from it.

BRIEF DESCRIPTION OF THE DRAWING

The figure shows a block diagram of an installation intended for the extemporaneous and continuous preparation of a dialysis solution.

DETAILED DESCRIPTION OF THE PREFERRED EMBODIMENTS

This installation is organized around a device consisting of a set of five cartridges, respectively referenced 1 to 5, arranged in parallel and each of which contains a salt of a substance necessary for the preparation of the dialyzate: sodium chloride, potassium chloride, calcium chloride, magnesium chloride, and sodium bicarbonate.

As specified in the preceding, the internal volume of each cartridge is partially occupied by semipermeable membrane fiber 6 essentially arranged along the longitudinal axis of said cartridges along the length of the first conduits, respectively referenced 11 to 15, of which a first end (indicated by an arrow) is connected to a source of purified water, not represented, which advantageously can be the source used to supply the circuit of water of the dialysis generator.

This water thus penetrates through a second end of said first conduits into each cartridge 1-5 and follows the path defined by the semipermeable membrane fibers. In a first step, the water thus carried diffuses to the interior of said cartridges by permeating through the membrane fibers, fills the volume of said cartridges, and is mixed with the powdered substances that envelope the fibers. The water thus loaded with salt then follows the path defined by the membrane fibers, with the concentrated solutions produced in each cartridge being directed to a point where they will be mixed.

For this purpose, at the outlet of cartridges 1-5 are the second conduits, respectively referenced 21 to 25, which are intended to collect the different concentrated solutions produced in order to carry them to a mixing point consisting of third conduit 10, which is connected to the fluid circuits of dialysis generator 100 by conduit 30 provided with pump 31.

One of the main advantages of the device of the invention is that it allows the composition of the dialyzate to be adapted to each clinical case, in a continuous manner during the dialysis session, as a function of the data belonging to each patient obtained in the course of treatment.

For this purpose, the device contains some first means of measuring the concentration of the solutions produced in each cartridge 1-5, consisting of conductivity cells arranged on second conduits 21-25 at the outlet of said cartridges and upstream from the third conduit or "mixing" conduit 10.

These conductivity cells, respectively referenced 210 to 250 in the attached drawing, thus transmit the information they collect to system 300 for running the installation that controls variable-flow-rate pumps, respectively referenced 110 to 150, mounted on first conduits 11-15, in order to regulate the flow rate of the introduction of purified water into each cartridge.

According to a variant of execution of the device of the invention, which is not illustrated, these pumps can be advantageously mounted on second conduits 21-25 in order to limit the load loss that can occur with pumps mounted on first conduits 11-15. Moreover, with a mounting of this type, the regulation of the flow rate is more precise and consistent.

In effect, as we have seen, each cartridge of the device of the invention contains a salt, and the variation in the flow rate of water alone allows for regulation of the transfer of the salt through the semipermeable membrane fiber with which these cartridges are equipped. This variation in the flow rate of water thus allows for modification of the concentration in terms of the salt of the solutions obtained.

The concentration of the solutions is furthermore controlled by second measurement means 101 arranged downstream from dialysis generator 100, for example, on the outlet of the dialyzate and/or in the blood circulation of the patient; these second measurement means act by the intermediary of automatic control system 300 on the pumps 110-150 for regulation of the flow rate of water.

For each salt, the coefficient of transfer by diffusion is determined. This coefficient consequently allows one to predict the concentration in terms of the salt at the outlet of each cartridge as a function of the flow rate of the water used. This water-flow rate is thus regulated as a function of the composition of the dialysis solution obtained in mixing conduit 10; this composition is adapted to each patient, particularly from the data collected during the session.

The sizes of the different cartridges, but also of the fibers that they contain, are determined so that the concentration, in millimoles of ions per liter, in the dialysis solution is within the following ranges:
from 135 to 150 mmol for the sodium ion,
from 1 to 3 mmol for the potassium ion,
from 0 to 1.75 mmol for the calcium ion, from 0.25 to 1 mmol for the magnesium ion,
from 25 to 35 mmol for the bicarbonate ion.

One will hereafter find two tables that indicate, as an example, the volume of the different cartridges, expressed in cm$^3$, for each salt included in the composition of a solution used for dialysis sessions with respective durations of 6 h and 8 h.

Table I

Dialysis session lasting 6 h.
Sodium chloride: 1270.80
Potassium chloride: 184.60
Calcium chloride: 184.60
Magnesium chloride: 276.60
Sodium bicarbonate: 1270.90

Table II

Dialysis session lasting 8 h.
Sodium chloride: 1694.50
Potassium chloride: 246.10
Calcium chloride: 246.20
Magnesium chloride: 368.80
Sodium bicarbonate: 1694.50

It should be added that the device of the invention also includes some means for supplying the dialysis solution circulating in conduit 10 with supplementary products such as glucose, amino, acids, and oligo-elements [oligosaccharides or oligopeptides]; these means are not described in more detail because their execution is within simple grasp of an expert in the field.

This device also includes a means for measuring the pH of the dialysis solution, consisting of cell 200 mounted on conduit 10 and connected to pH-meter 201, which thus allows one to adjust the pH of the mixture circulating in said conduit to a physiological value.

A device of this type is necessarily equipped with a means of thermal regulation in order to maintain the dialysis solution at an appropriate clinical temperature, for example, at a temperature of 37° C.

These means of thermal regulation can, in a known way, include, for example, an electrical resistance device associated with mixing conduit 10.

It is obvious that the device that has just been described can be the object of various modifications without deeply disrupting its design. Thus, for example, the cartridges can be grouped in enclosure 7, represented by broken lines, provided with a single entrance of water and a valve system allowing for the selective supply, with water, of one or another of the other said cartridges, with the essence being to keep the modular character of the device, which results in particular from the possibility of adding or removing cartridges containing different substances as a function of the nature of the final solution that one wishes to obtain.

I claim:

1. A device for the preparation of a solution for medical use by the dissolution of several substances in powder form in a carrier fluid, comprising:
    a plurality of cells, each containing at least one of said substances in powder form,
    at least one first conduit having a first end communicating with a source of carrier fluid and a second end communicating with each of said plurality of said cells for introducing said carrier fluid into each of said plurality of said cells to produce aqueous solutions in each of said plurality of said cells, at least one second conduit communicating with each of said plurality of said cells for bringing said aqueous solutions produced in each of said plurality of said cells to a mixing point located upstream from a site of utilization, at least one measurement means mounted upstream from said mixing point, for measuring the concentration of said aqueous solutions produced in each of said plurality of said cells, and at least one means for regulating flow rate of said carrier fluid into each of said plurality of said cells in order to modify the concentration of said aqueous solutions in each of said plurality of said cells in response at least to concentration measurements provided by said measurement means, control means for collecting said concentration measurements from said measurement means and for operating said flow rate regulation means in order to modify the concentration of said aqueous solutions in each of said plurality of said cells in response at least to concentration measurements provided by said measurement means.

2. A device according to claim 1, wherein each of said cells contains a means for diffusion and circulation of said carrier fluid in said plurality of said cells.

3. A device for extemporaneous and continuous preparation of a solution for use in combination with a dialysis circuit by the dissolution of several substances in powder form in water, comprising:

a plurality of independent cartridges, each containing at least one salt of a substance necessary for the preparation of said solution, said at least one salt being selected from the group consisting of sodium chloride, potassium chloride, calcium chloride, magnesium chloride and sodium bicarbonate, at least one first conduit communicating with an inlet of each of said plurality of said cartridges for introducing water into said cartridges for producing solute in said cartridges, at least one second conduit communicating with an outlet from said cartridges for bringing said solute to a mixing point located upstream from the dialysis circuit, at least one measurement means mounted on said second conduit upstream from said mixing point, for measuring concentration of said solute produced in said cartridges, and at least one means of flow-rate regulation for regulating the flow rate of the water into each of said plurality of said cartridges in order to modify the concentration of said solute in response to the concentration measurements provided by said at least one measurement means, control means for collecting said concentration measurements from said at least one measurement means and for operating said flow-rate regulation means in order to modify the concentration of said solute in each of said cartridges in response to concentration measurements provided by said at least one measurement means.

4. A device according to claim 3, wherein each of said plurality of said cartridges contains means of diffusion and of circulation of water between said inlet and outlet of each of said plurality of said cartridges.

5. A device according to claim 4, wherein said diffusion and circulation means is disposed substantially along a longitudinal axis of each of said plurality of said cartridges.

6. A device according to claim 4, wherein said diffusion and circulation means comprises at least one semipermeable membrane fiber.

7. A device according to claim 6, wherein sizes of each of said plurality of cartridges and fibers are selected wherein the concentration, in millimoles of ions per liter, in the dialysis solution obtained is within the following ranges:

from 135 to 150 mmol of sodium ion,
from 1 to 3 mmol of potassium ion,
from 0 to 1.75 mmol of calcium ion,
from 0.25 to 1 mmol of magnesium ion,
from 25 to 35 mmol of bicarbonate ion.

8. A device according to claim 3, wherein said means for regulating the flow rate of the water is mounted on said first conduit.

9. A device according to claim 3, wherein said means for regulating the flow rate of the water is mounted on said second conduit.

10. A device according to claim 3, wherein said mixing point comprises third conduit mounted at an inlet of said dialysis circuit.

11. A device according to claim 3, wherein one of said at least one measurement means comprises conductivity cell.

12. A device according to claim 3, wherein said means for regulating the flow rate comprise variable-flow-rate pumps.

13. A device according to claim 10, further comprising means for measuring pH of a mixture in said third conduit.

14. A device according to claim 10, further comprising means for introducing into said third conduit, at least one substance selected from the group consisting of glucose, amino acids and oligo-elements.

15. A device according to claim 3, further comprising means for thermally regulating the solute at a selected temperature.

16. A device according to claim 3, wherein each of said plurality of cartridges are housed in an enclosure.

17. A device according to claim 1, further comprising second measurement means to be mounted downstream from the site of utilization.

18. A device according to claim 3, further comprising second measurement means to be mounted downstream from the dialysis circuit.

* * * * *